US00RE37515B1

(19) United States
(12) Reissued Patent
Mitchell

(10) Patent Number: US RE37,515 E
(45) **Date of Reissued Patent: *Jan. 15, 2002**

(54) REJUVENATION OF HYDROCARBON SYNTHESIS CATALYST

(75) Inventor: Willard N. Mitchell, Baton Rouge, LA (US)

(73) Assignee: Exxon Research and Engineering Company, Annandale, NJ (US)

( * ) Notice: This patent issued on a continued prosecution application filed under 37 CFR 1.53(d), and is subject to the twenty year patent term provisions of 35 U.S.C. 154(a)(2).

(21) Appl. No.: 09/133,419

(22) Filed: Aug. 13, 1998

Related U.S. Patent Documents

Reissue of:
(64) Patent No.: 5,283,216
Issued: Feb. 1, 1994
Appl. No.: 07/949,934
Filed: Sep. 24, 1992

(51) Int. Cl.[7] ..... B01J 38/58; B01J 38/56; B01J 38/10; C07C 1/04

(52) U.S. Cl. ..... 502/30; 502/31; 502/53; 518/700; 518/709; 518/710; 518/715; 518/719

(58) Field of Search ..... 502/29, 30, 31, 502/53, 22; 518/700, 709, 710, 715, 719; 208/950

(56) References Cited

U.S. PATENT DOCUMENTS

| | | | | |
|---|---|---|---|---|
| 2,159,140 A | | 5/1939 | Eckell | 518/710 |
| 2,238,726 A | | 4/1941 | Feisst et al. | 518/709 |
| 2,259,961 A | | 10/1941 | Mydleton | 518/710 |
| 4,670,472 A | * | 6/1987 | Dyer et al. | 518/700 |
| 4,892,646 A | | 1/1990 | Venkat | 208/111.35 |

OTHER PUBLICATIONS

MPEP 1412.03, p. 1400–12, Feb. 2000.*
Vannice, M.A., Journal of Catalysis 37, 449–461 (1975). No month.
Emmett, Paul H., Catalysis vol. IV, pp. 103–108, 1956. No month.

* cited by examiner

*Primary Examiner*—John F. Niebling
*Assistant Examiner*—Alexander G. Ghyka
(74) *Attorney, Agent, or Firm*—Jay Simon

(57) ABSTRACT

A cobalt- or ruthenium-containing hydrocarbon synthesis catalyst, subjected to short term, reversible, partial deactivation in a slurry synthesis process can be rejuvenated, i.e., at least about 80+% catalyst activity recovery, by treating the catalyst in the presence of liquid hydrocarbons, preferably the slurry hydrocarbons, with hydrogen at elevated temperatures and pressures.

13 Claims, 1 Drawing Sheet

REJUVENATION OF HYDROCARBON SYNTHESIS CATALYST

Matter enclosed in heavy brackets [ ] appears in the original patent but forms no part of this reissue specification; matter printed in italics indicates the additions made by reissue.

FIELD OF THE INVENTION

This invention relates to a method for rejuvenating or reactivating a Group VIII metal containing hydrocarbon synthesis catalyst that has undergone short term, reversible deactivation as a result of slurry phase hydrocarbon synthesis operation. More particularly, the rejuvenation method comprises treating the partially deactivated catalyst with hydrogen in the presence of hydrocarbon containing liquids, preferably the slurry phase.

BACKGROUND OF THE INVENTION

During hydrocarbon synthesis the conversion of CO decreased with time. This may be due to the deactivation of the catalyst or slurry liquid properties charging limiting mass transfer. Nevertheless, the mode of deactivation of hydrocarbon synthesis catalysts is not too well understood, but is believed to be related, at least somewhat, to the mode in which the hydrocarbon synthesis is carried out; e.g., a different deactivation mode is likely present for catalyst in fixed bed operations than the deactivation mode for slurry phase operations. Thus, fixed bed processes are essentially plug flow operations involving reactant gradients as they progress through the catalyst bed whereas slurry phase operations involve sufficient backmixing tending towards a more uniform distribution of reactants and products throughout the slurry phase. For example, in a fixed bed water would not be present at the start of the reaction and would build up as the reaction progressed through the bed. However, in a slurry phase, e.g., in a slurry bubble column, because of back mixing effects, water will be present throughout the reaction slurry bed. Consequently, deactivation modes, dependent to any degree on the presence of water, will be different for fixed bed and slurry phase processes.

Hydrogen rejuvenation treatments have been employed with catalysts operated in fixed beds with, at best, limited and inconsistent recovery of hydrocarbon synthesis activity. In one case, steady state operation in the fixed bed had not been achieved, in other cases excessively high temperatures were employed, and still in other cases the hydrogen treatment was in the absence or substantial absence of hydrocarbon liquids.

SUMMARY OF THE INVENTION

Essentially complete reversal of short term, reversible catalyst deactivation of a cobalt- or ruthenium-containing catalyst, partially deactivated in slurry phase hydrocarbon synthesis operation, can be obtained by hydrogen treating, in the absence of CO, the partially deactivated catalyst in the presence of liquid hydrocarbons, preferably slurry phase hydrocarbons. The hydrogen treating which may be referred to as a catalyst rejuvenation method, allows for the recovery of a substantial portion of the initial catalyst activity, that is, start of run activity. Thus, at least about 80+% preferably at least about 90+% of initial catalyst activity is recovered, and the rejuvenation is carried out at elevated temperatures and pressures, and with sufficient liquid for fully immersing the catalyst. Generally, the rejuvenation is effected at hydrocarbon synthesis pressures, and temperatures no more than about 100° F. (approximately 40° C.) below reaction temperatures. The hydrogen treatment may be performed in situ or in a separate treatment vessel. Preferably, hydrogen is injected into a slurry of hydrocarbons and catalyst, preferably with sufficient energy from the hydrogen alone, to disperse the catalyst particles in the liquid. The hydrogen is also free of oxygen and can be neat or mixed with inerts such as $N_2$, $CO_2$, $CH_4$, preferably nitrogen.

In a preferred embodiment, the hydrogen treatment involves conducting a slurry phase, hydrocarbons synthesis process, primarily to produce $C_5$+hydrocarbons in which the flow of synthesis gas feed is periodically interrupted, and during those interruptions the slurried catalyst is treated with hydrogen for a period sufficient to recover all or substantially all of the initial catalyst activity. After rejuvenation, the catalyst slurry is returned to hydrocarbon synthesis operation, e.g., in a bubble column slurry reactor.

The degree of deactivation that triggers the rejuvenation can be pre-set by the operator based on a wide variety of factors known to those skilled in the art. Also, the rejuvenation can be carried out at any time and for any reason, e.g., unexpected reversible unit upsets.

Short term, reversible catalyst deactivation leading to rejuvenation preferably occurs during that period in which catalyst activity decreases to 50% of its initial, or start of run, activity, i.e., the apparent half life of the catalyst. In this discussion, catalyst activity can be considered as a measure of rate of CO conversion, and can be represented by volumetric catalyst productivity, i.e., vol CO converted/hr/vol of catalyst. Depending on the nature and severity of the process, apparent half life usually occurs in less than about 150 days on stream at hydrocarbon synthesis conditions and at design feed rates.

While catalyst activity resulting from normal operations is short term and reversible, and can be substantially completely recovered by hydrogen treatment, some types of catalyst deactivation are irreversible and not susceptible to activity recovery via the rejuvenation technique, e.g., metal agglomeration, or catalyst poisoning by virtue of graphitic carbon laydown, sulfur, sodium or other catalyst poisons.

The period of the hydrogen rejuvenation treatment should be limited to that period sufficient to maximize the recovery of catalyst activity, thereby avoiding the possibility of hydrogenolysis of the liquid with attendant carbon formation and potentially permanent catalyst deactivation.

DETAILED DESCRIPTION OF THE INVENTION

Figure 1:
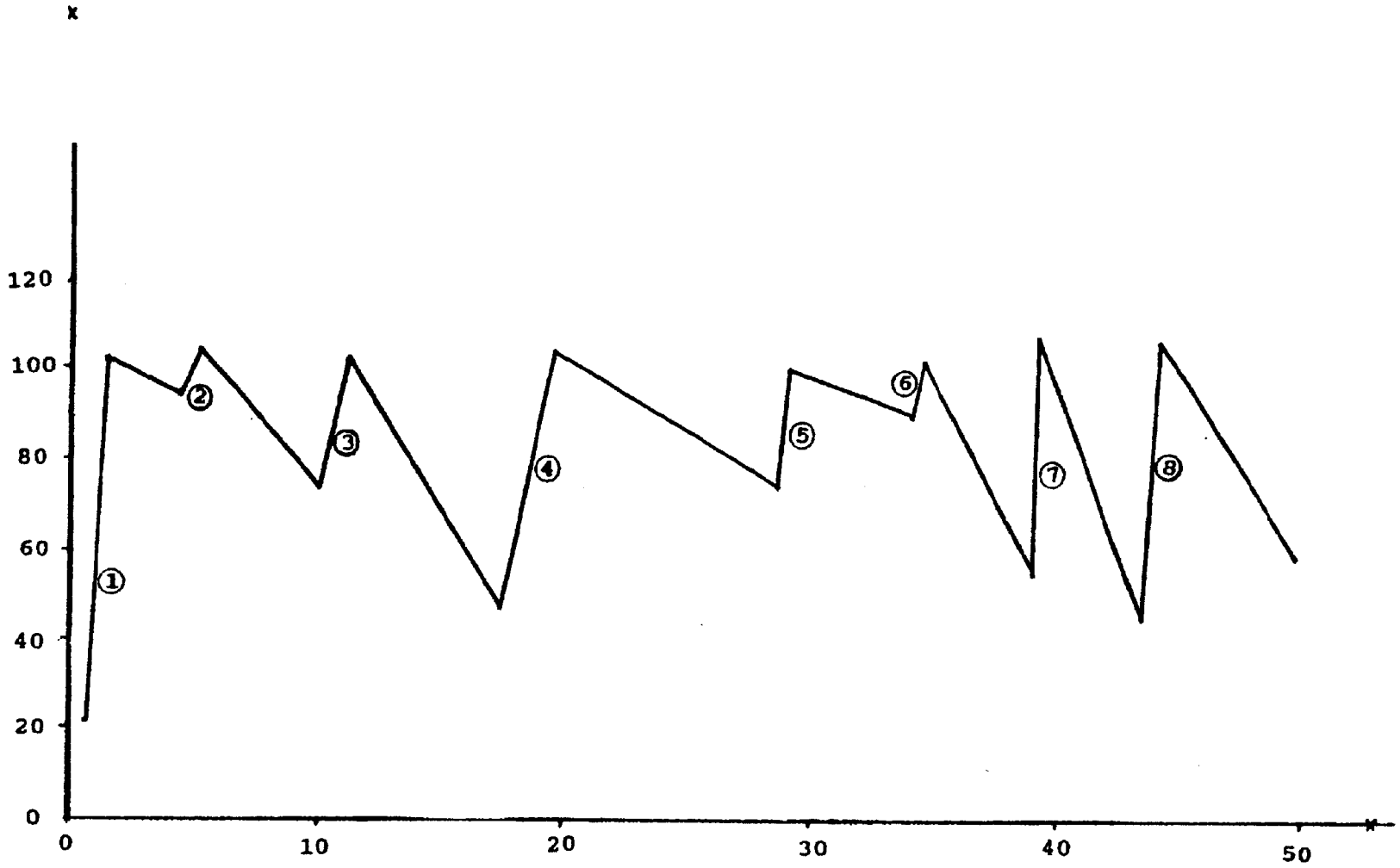
FIG. 1 is a plot of relative volumetric productivity representing activity (ordinate) v. days on stream (abscissa) for a run showing hydrogen rejuvenation of a cobalt-containing hydrocarbon synthesis catalyst. For this example deactivation was relatively severe resulting in relatively short catalyst half-life.

Slurry phase hydrocarbon synthesis processes are carried out at elevated temperatures and pressures, typical of Fischer-Tropsch processes. Thus, pressures may range from 1–100 atmospheres, preferably 5–40 atmospheres, more preferably 10–25 atmospheres. Temperatures may range from about 175° C. to 450° C., preferably 175° C. to 425° C., more preferably 175° C. to 300° C., and hydrogen to carbon monoxide ratios in the feed gas may range from about 1.5 to 4.0, preferably about 1.7 to 2.5. The slurry usually comprises about 10 wt. % to 50 wt. % catalyst solids, preferably 30 wt. % to 40 wt. % catalysts solids. The catalyst can be maintained in suspension in the slurry liquid by a combination of product recycle liquid, slurry recycle liquid, and injected recycle product gas, and synthesis gas feed. Preferably, the feed gas provides the majority of energy, more preferably, essentially all of the energy required for maintaining the catalyst suspended in the slurry liquid.

For ease of operation the rejuvenation technique can be effected at hydrocarbon synthesis reaction conditions, as known to those skilled in art and described hereinabove, but preferably at elevated temperatures and pressures. Typically, the temperature may range to about 100° F. (approximately 40° C.) below synthesis conditions while pressures are maintained at or about synthesis conditions.

Hydrogen treat rates during rejuvenation typically range from about 10–50 SCF/lb of catalyst, preferably about 15–30 SCF/lb of catalyst; or on another basis from about 500–5000, preferably 1500–3000 SCF/lb hydrocarbons in the slurry liquid. The time for rejuvenation varies with hydrogen treat rates, temperatures, etc., but is usually accomplished in about 0.25–24 hours, preferably about 0.5–2 hours. The hydrogen may be plant or refinery hydrogen and is used as received. In this condition it is substantially free of moisture, that is, less than about 0.5 wt. % $H_2O$ in the hydrogen. The hydrogen is also free of oxygen.

While the mechanism for rejuvenation is uncertain, its fact is clearly demonstrable. However, those skilled in the art will not continue the rejuvenation procedure beyond the point of maximum activity recovery (a point easily determined with but a few experiments) because of the possibility that the liquid hydrocarbons will undergo hydrogenolysis with attendant serious consequences for the catalyst. Perhaps, the fact that slurry phase hydrogen rejuvenation had not been attempted previously was the widespread belief that hydrogen treatment at elevated temperatures and pressures, and the presence of hydrocarbons and of a hydrogenation catalyst (Fischer-Tropsch synthesis can be viewed as the hydrogenation of CO) would lead to hydrogenolysis of the liquids resulting in methane formation, the most unwanted product in Fischer-Tropsch synthesis, and attendant "coke" formation that would deleteriously affect catalyst life and activity.

The slurry liquid is a hydrocarbon, liquid at reaction conditions, generally inert and a good solvent for synthesis gas. Typically, the slurry is the product of the reaction and contains $C_{5+}$ hydrocarbons, usually $C_5$–$C_{50}$ hydrocarbons. However, the slurry liquid is comprised primarily of high boiling paraffins, with small amounts of primary and secondary alcohols, acids and esters or mixtures thereof. The high boiling paraffins include primarily $C_{10\text{-}C50}$ linear hydrocarbons. The slurry liquid can contain hetero oxygen atoms in the molecular structure but not sulfur, phosphorus, arsenic or antimony atoms since these act as poisons in hydrocarbon synthesis processes. Examples of specific slurry materials are: dodecane, tetradecane, hexadecane, octadecane, hexatriacontane, tetracosane, octacosane, dotriacontane, tetracontane, tetratetracontane. Preferred slurry materials are Fischer-Tropsch waxes and $C_{16}$–$C_{18}$ alkyl hydrocarbons.

The catalyst may be a Group VIII metal containing catalyst, preferably iron, cobalt, or ruthenium, more preferably cobalt or ruthenium containing, and most preferably cobalt, and is preferably a supported catalyst wherein the support is selected from the group of difficulty reducible inorganic oxides of Groups III, IV, V, VI, and VIII of the Periodic Chart of Elements. Preferred supports are Group IVB oxides, particularly those having a surface area of 100 $m^2$/gm or less preferably 70 $m^2$/gm or less. A particularly preferred support contains primarily rutile titania.

Promoters may be added to the catalyst, for example, ruthenium, rhenium, hafnium, cerium, and zirconium. Typically, the cobalt is present in catalytically active amounts, e.g., 1–50 wt. %, preferably about 2–40 wt. %, more preferably 2–25 wt. %. Promoters, when they are present are typically present in amounts of less than the cobalt (except for ruthenium which may be present in co-equal amounts). However, the promoter:cobalt ratio should be at least about 0.1/1. Preferred promoters are rhenium and hafnium.

Catalyst preparation may be accomplished by a variety of techniques, although catalyst preparation does not play a part in this invention and the hydrogen treatment disclosed herein will improve the activity of the hydrocarbon synthesis catalyst however it is prepared.

A typical catalyst preparation may involve impregnation, by incipient wetness or other known techniques of, e.g., a cobalt nitrate salt onto a titania, silica, or alumina support, optionally followed or proceeded by impregnation with a promoter material, e.g., perrhenic acid. Excess liquid is removed and the catalyst precursor dried at 100° C. to 125° C. Following drying or as a continuation thereof, the catalyst is calcined at about 300° C.–500° C. to convert the salt or compound to its corresponding oxide(s). The oxide is then reduced by treatment with hydrogen or a hydrogen containing gas at about 300° C.–500° C. for a period of time sufficient to substantially reduce the oxide to the elemental or catalytic form of the metal. Some prefer an additional cycle of oxidation/reduction. Another, and sometimes preferred method for catalyst preparation is disclosed in U.S. Pat. No. 4,621,072 incorporated herein by reference. Nevertheless, the catalyst subjected to the slurry phase hydrogen treatment of this invention is one that has already been reduced by conventional means. Thus, the catalyst has, essentially, not been previously used in hydrocarbon synthesis.

EXAMPLES

The following examples will further serve to illustrate this invention:

In a preferred embodiment the hydrocarbon synthesis process is conducted in a slurry mode at normal reaction conditions, thereby subjecting the catalyst to reversible deactivation. At an appropriate time, e.g., catalyst half life, or periodically during the operation, the hydrogen and carbon monoxide feed is replaced with hydrogen or a hydrogen containing gas and catalyst rejuvenation is carried out at reaction pressures and temperatures in the range of reaction temperature to about 100° F. below reaction temperature. Thus, the process becomes a continuous process with periodic interruptions for catalyst rejuvenation.

Catalyst preparation may be accomplished by a variety of techniques, although catalyst preparation does not play a part in this invention and the hydrogen treatment disclosed herein will improve the activity of the hydrocarbon synthesis catalyst however it is prepared.

A typical catalyst preparation may involve impregnation, by incipient wetness or other known techniques of, e.g., a cobalt nitrate salt onto a titania, silica, or alumina support, optionally followed or proceeded by impregnation with a promoter material, e.g., perrhenic acid. Excess liquid is removed and the catalyst precursor dried at 100° C. to 125°

C. Following drying or as a continuation thereof, the catalyst is calcined at about 300° C.–500° C. to convert the salt or compound to its corresponding oxide(s). The oxide is then reduced by treatment with hydrogen or a hydrogen containing gas at about 300° C.–500° C. for a period of time sufficient to substantially reduce the oxide to the elemental or catalytic form of the metal. Some prefer an additional cycle of oxidation/reduction. Another, and sometimes preferred method for catalyst preparation is disclosed in U.S. Pat. No. 4,621,072 incorporated herein by reference.

EXAMPLE 1

In a hydrocarbon synthesis process demonstration unit, catalyst rejuvenation of short term, reversible deactivation due to operation in a slurry hydrocarbon synthesis mode, was effected over several periods. The unit was operated with 2200 lbs of 12 wt. % cobalt, on a titania support with 6 wt. % $Al_2O_3$ as a binder material. Catalyst particle size was 10 to 90 microns. The unit was operating with 2/1 hydrogen:carbon monoxide feed at a rate of 10–17 cm/sec a temperature of 420° F.–440° F. (215° C.–227° C.) and at 285 psig. Hydrogen treatment was effected at various stages of the run. The first three treatments established the maximum volumetric catalyst productivity (initial activity) for this run (expressed as 100% relative productivity). Treatment 7 was a typical rejuvenation treatment in accordance with this invention. After eliminating the flow of synthesis gas, hydrogen and nitrogen, 50–75% hydrogen in nitrogen, were injected into the unit at about 8–10 cm/sec gas velocity. Treatment 7 was carried out for 1¼ hours. Clearly, after the treatment and reintroduction of synthesis gas feed, the relative productivity recovered from 53% relative productivity to about 102% relative productivity. This was a complete recovery of catalyst productivity.

Other rejuvenation treatments are depicted sequentially by a number in a circle in FIG. 1, and all rejuvenation treatments showed the recovery of substantial catalyst activity.

What is claimed is:

1. A method for rejuvenating a partially deactivated, Group VIII metal containing Fischer-Tropsch catalyst having an initial catalyst activity which comprises: suspending the catalyst in slurry liquid hydrocarbons and treating the suspended catalyst with hydrogen or a hydrogen containing gas at elevated temperatures and pressures and recovering a substantial portion of the initial catalyst activity.

2. The method of claim 1 wherein the catalyst contains iron, cobalt, or ruthenium.

3. The method of claim 2 wherein rejuvenation is effected at temperatures ranging from 135° C. to 425° C.

4. The method of claim 1 wherein at least a portion of the energy required for maintaining the catalyst in a suspension is supplied by injection of hydrogen containing gas.

5. The method of claim 1 wherein deactivation resulted from a slurry phase hydrocarbon synthesis process.

6. The method of claim 1 wherein the pressure is about hydrocarbon synthesis pressure and the temperature ranges from hydrocarbon synthesis temperature to about 40° C. below hydrocarbon synthesis temperature.

7. The method of claim 6 wherein at least about 90% of initial catalyst productivity is recovered.

8. The method of claim 6 wherein the catalyst contains catalytically active amounts of cobalt.

9. The method of claim 8 wherein the catalyst is cobalt supported on a Group IVB oxide.

10. The method of claim 9 wherein the catalyst is a supported cobalt catalyst.

*11. A method for producing liquid $C_5$ plus hydrocarbons in a slurry phase reactor with catalyst comprising rejuvenating said catalyst in situ according to the method of claim 1.*

*12. The method of claim 11 wherein said $C_{5+}$ hydrocarbons comprise $C_5$–$C_{50}$ hydrocarbons.*

*13. The method of claim 11 wherein said $C_{5+}$ hydrocarbons comprise Fischer-Tropsch waxes.*

* * * * *